US009234857B2

(12) United States Patent
Niebel et al.

(10) Patent No.: US 9,234,857 B2
(45) Date of Patent: Jan. 12, 2016

(54) METHOD AND APPARATUS PROVIDING TEMPERATURE UNIFORMITY

(71) Applicant: FIRST SOLAR, INC, Perrysburg, OH (US)

(72) Inventors: Kevin Niebel, Toledo, OH (US); James Sorensen, Whitehouse, OH (US); Patrick Buehler, Pemberville, OH (US)

(73) Assignee: FIRST SOLAR, INC., Perrysburg, OH (US)

( * ) Notice: Subject to any disclaimer, the term of this patent is extended or adjusted under 35 U.S.C. 154(b) by 366 days.

(21) Appl. No.: 13/676,912

(22) Filed: Nov. 14, 2012

(65) Prior Publication Data

US 2013/0121370 A1    May 16, 2013

Related U.S. Application Data

(60) Provisional application No. 61/559,459, filed on Nov. 14, 2011.

(51) Int. Cl.
| | |
|---|---|
| *G01K 13/00* | (2006.01) |
| *G01K 1/00* | (2006.01) |
| *G01K 7/00* | (2006.01) |
| *G01N 25/18* | (2006.01) |
| *H02S 50/10* | (2014.01) |

(52) U.S. Cl.
CPC .............. *G01N 25/18* (2013.01); *H02S 50/10* (2014.12)

(58) Field of Classification Search
USPC .......................... 374/208, 179, 141, 166, 44
See application file for complete search history.

(56) References Cited

U.S. PATENT DOCUMENTS

| | | | |
|---|---|---|---|
| 4,011,856 A | 3/1977 | Gallagher | |
| 4,090,071 A * | 5/1978 | McCarter | 250/238 |
| 5,646,050 A | 7/1997 | Li et al. | |
| 7,429,718 B2 | 9/2008 | Inagawa et al. | |
| 7,910,399 B1 * | 3/2011 | Wieting | 438/96 |
| 7,947,524 B2 | 5/2011 | Wieting | |
| 2004/0086021 A1* | 5/2004 | Litwin | 374/120 |
| 2005/0120811 A1* | 6/2005 | Hardcastle | 73/865.6 |
| 2007/0039942 A1 | 2/2007 | Leung et al. | |
| 2007/0128905 A1 | 6/2007 | Speakman | |
| 2009/0000662 A1 | 1/2009 | Harwood et al. | |
| 2009/0072837 A1 | 3/2009 | Kushiya et al. | |
| 2010/0000594 A1 | 1/2010 | Zalusky et al. | |
| 2010/0046575 A1* | 2/2010 | Hebert et al. | 374/57 |

(Continued)

FOREIGN PATENT DOCUMENTS

| | | | |
|---|---|---|---|
| WO | WO 2008/094555 A2 | 8/2008 | |
| WO | WO 2011/056672 A2 | 5/2011 | |
| WO | WO 2011/063890 A2 | 6/2011 | |

OTHER PUBLICATIONS

Y. Lu et al., "Study of Thin-film Silicon Solar Cells at Irradiances Above Ten Thousand Suns," Journal of Physics: Conference Series vol. 253, pp. 1-6, 2010.

(Continued)

*Primary Examiner* — Mirellys Jagan
(74) *Attorney, Agent, or Firm* — Dickstein Shapiro LLP (57) ABSTRACT

A temperature uniformity device controls the temperature and temperature uniformity of an object such as a photovoltaic module undergoing testing. The temperature uniformity device includes a thermal conductivity device and a pliable thermally conductive interface material inserted between the object and the thermal conductivity device.

22 Claims, 7 Drawing Sheets

(56) References Cited

U.S. PATENT DOCUMENTS

| | | |
|---|---|---|
| 2010/0073011 A1 | 3/2010 | Svidenko et al. |
| 2010/0136715 A1* | 6/2010 | Sopori et al. ............... 438/14 |
| 2010/0147347 A1 | 6/2010 | Dyreby et al. |
| 2010/0288333 A1 | 11/2010 | Temchenko et al. |
| 2011/0044000 A1 | 2/2011 | Minano et al. |
| 2011/0103423 A1* | 5/2011 | Hsu et al. .................... 374/43 |
| 2012/0063485 A1* | 3/2012 | Reed ............................. 374/5 |
| 2012/0268149 A1* | 10/2012 | Buehler et al. .......... 324/750.08 |

OTHER PUBLICATIONS

J. A. del Cueto et al., "Stabilization of High Efficiency CdTe Photovoltaic Modules in Controlled Indoor Light Soaking," National Renewable Energy Laboratory, National Center for Photovoltaics and Solar Program Reviewing Meeting, Denver, Colorado, pp. 1-4, Mar. 24-26, 2003.

* cited by examiner

METHOD AND APPARATUS PROVIDING TEMPERATURE UNIFORMITY

FIELD OF THE INVENTION

Embodiments of the invention relate to a temperature uniformity device for controlling the temperature and the temperature uniformity of an object, such as a photovoltaic module.

BACKGROUND OF THE INVENTION

A photovoltaic module, also known as a solar panel, is a device that converts the energy of sunlight directly into electricity by the photovoltaic effect. A photovoltaic module includes a plurality of photovoltaic cells, also known as solar cells, for example, crystalline silicon cells or thin-film cells. Stable photovoltaic energy production depends on many factors, some of which include specific semiconductor materials, interconnect technologies, and module encapsulation. To improve long term reliability, life testing can be performed on photovoltaic modules to determine their life cycle in the field, using various temperatures and biasing conditions. A module's open circuit voltage $V_{oc}$ (i.e., the maximum voltage from a cell when the net current through the module is zero), short-circuit current $I_{sc}$ (i.e., the maximum current from a cell when the voltage across the cell is zero), fill factor (i.e., the ratio of the maximum power from a cell to the product of $V_{oc}$ and $I_{sc}$ and cell efficiency can be observed under controlled environmental conditions in, for example, an accelerated, indoor light soaking chamber (or LSC).

During the testing process under controlled environmental conditions, photovoltaic modules to be tested are placed in a LSC preheated to a set point temperature and exposed to simulated light for extended periods of time. The set point is the temperature at which the control system of a LSC will hold the photovoltaic modules while under test. Conventional light soaking systems allow temperature control over a range from 50° Celsius to 90° Celsius. A solar simulator such as high power metal halide lamps, gas lasers, Xenon discharge lights or other light sources can simulate light exposure on the photovoltaic modules in the chamber. An illumination level of 100,000 lux of illumination over a 300 $mm^2$ area is comparable to 1 sun light intensity exposure. Life testing can be performed with irradiance intensities in the range of 600 $W/m^2$ to 1500 $W/m^2$, however, other intensities could be employed. As an example of a test condition, life testing can be performed at so-called Standard Test Conditions (STC), which corresponds to a light intensity of 1000 $W/m^2$ at 25° Celsius, with a reference solar spectral irradiance called Air Mass 1.5 (AM 1.5). The test duration typically ranges from 24 hours to 300 hours; however, other test &rations could be employed.

The overall photovoltaic module temperature and the temperature uniformity across the module need to be carefully controlled in order to accurately simulate module performance during life testing. Temperature uniformity of a photovoltaic module refers to the variation of the temperature over a surface of the module. Less variation in the temperature over the surface of the module results in a more accurate test. Moreover, the overall module temperature should be maintained as close to a predetermined set point temperature as possible.

Controlling the temperature and the temperature uniformity over the tested photovoltaic module is difficult with existing light soaking systems. Conventional light soaking systems, such as the one described in U.S. patent application Ser. No. 12/564,697 and filed on Jun. 30, 2009, primarily use fans to keep a constant air flow under and over the photovoltaic module during testing to maintain a set temperature uniformly over the module. Nevertheless, hot and cold spots on and within the module may still exist as it is difficult for such systems to effectively control the module temperature for set point temperatures below 50° Celsius. It is also difficult for such systems to achieve a temperature uniformity less than +/−7° Celsius across the photovoltaic module.

Accordingly, there is a need for a light soaking system that maintains better temperature uniformity across a photovoltaic module being tested and which can operate over a wider range of set point temperatures.

DETAILED DESCRIPTION OF THE INVENTION

In the following detailed description, reference is made to the accompanying drawings which form a part hereof, and in which is shown by way of illustration specific embodiments that may be practiced. It should be understood that like reference numbers represent like elements throughout the drawings. These embodiments are described in sufficient detail to enable those skilled in the art to make and use them, and it is to be understood that structural, material, electrical, and procedural changes may be made to the specific embodiments disclosed, only some of which are discussed in detail below.

Described herein are embodiments of a temperature uniformity device for controlling the temperature and the temperature uniformity of an object such as a photovoltaic module undergoing testing in a dedicated test room, or other space with controlled environmental conditions. Embodiments of the temperature uniformity device include a thermal conductivity device filled with a fluid medium that is circulated and an interface material in contact with the thermal conductivity device. A photovoltaic module under test can be placed in contact with the interface material.

The temperature uniformity device can maintain the overall temperature of the photovoltaic module to within +/−2° Celsius of a set point temperature. The temperature uniformity device can also control temperature uniformity to less than +/−4° Celsius across the module. The set point temperature can be any temperature within the range of 0° Celsius to 90° Celsius.

Figure 1A:
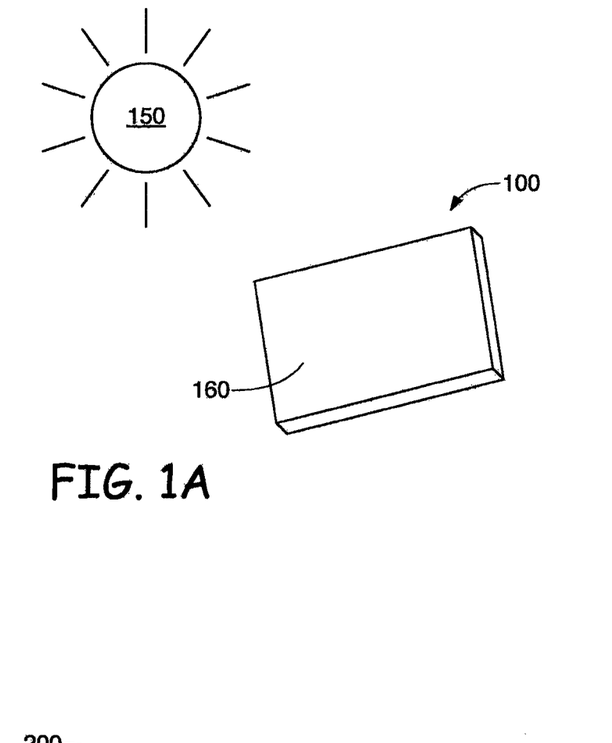
FIGS. 1A and 1B respectively show a top view and a bottom view of a photovoltaic module in accordance with a disclosed embodiment.
Figure 1B:
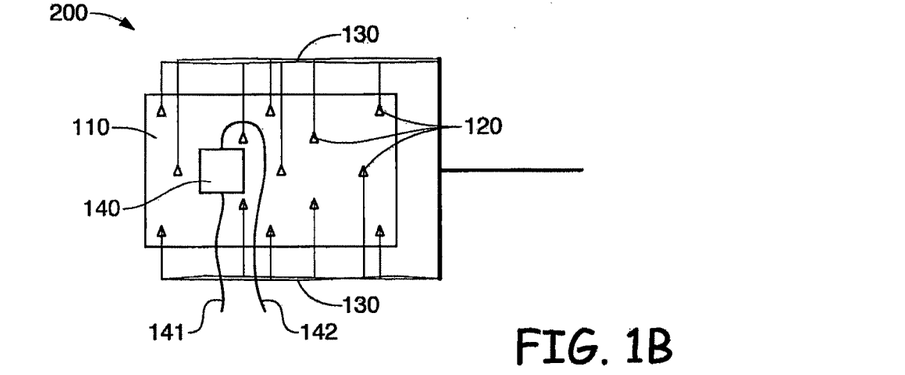

FIGS. 1A and 1B respectively show a top view and a bottom view of an example of a basic photovoltaic module 100. The photovoltaic module 100 has a front cover plate 160 on the top side that faces a light source 150, such as the sun. As shown in FIG. 1B, module 100 also has a back cover plate 110 on the bottom side and a cord plate 140 affixed to the back cover plate 110. For testing purposes, multiple temperature sensors 120 can be externally coupled to the back cover plate 110. Module 100 can represent a plurality of like constructed photovoltaic modules. Alternatively, for a test module which represents a plurality of like constructed photovoltaic modules, the temperature sensors 120 of the test module can be attached to an internal surface of the photovoltaic module 100. For example, the photovoltaic module 100 can have a back contact layer. An insulating tape can be used to attach a lead foil across a surface of the back contact layer. Each sensor 120, whether internal or external, measures the module temperature at a respective location. The electrical wires 130 of sensors 120 can be connected to a controller to communicate the module temperature at the locations of the sensors 120.

Module 100 may contain any number of photovoltaic cells and can be any size including, for example, a 4 feet by 2 feet photovoltaic module having an internal array of photovoltaic cells. It should be noted that the illustrated photovoltaic module 100 is not intended to be considered a limitation on the types of photovoltaic modules to which the present invention may be applied, but rather a convenient representation for the following description. The photovoltaic module 100 may employ any type of known photocells, including thin-film, silicon, or other types of solar cells.

The back cover plate 110 serves as a protective cover for the rear side of the module 100. The back cover plate 110 may include a transparent protective material such as borosilicate glass, soda lime glass, or polycarbonate. Alternately, the back cover plate 110 may be a non-transparent material such as Coveme's APYE or 3M's polymer back sheet.

The cord plate 140 may serve as a junction box and receive one or more external electrical wires 141, 142 which connect to the internal cells of the module 100. The wires 141, 142 may be connected to electrical devices of a testing apparatus or to other modules under test. The cord plate 140 may be constructed from polycarbonate, plastic, resin, rubber, or any other suitable material.

Temperature sensors 120 can be thin film thermocouple devices, resistance temperature detectors (RTDs), thermistors or any other contact temperature sensing device. Alternatively, non-contact temperature sensors such as pyrometers and spectrometers can be used to measure the surface temperature of the photovoltaic module 100. Other external module components such as cables and connectors that may be needed to transport generated electricity from the photovoltaic module in the field are not shown in FIGS. 1A and 1B for sake of simplicity.

Figure 2A:
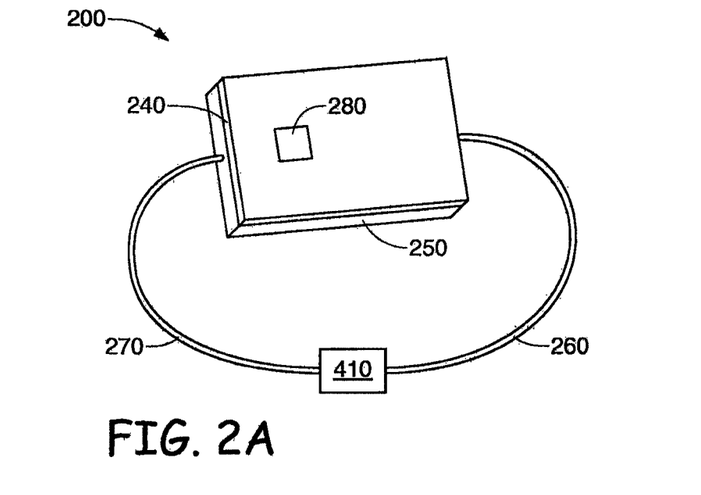
FIGS. 2A, 2B and 2C respectively show a perspective view, a cross-sectional view, and a bottom view of a temperature uniformity device in accordance with a disclosed embodiment.
Figure 2B:
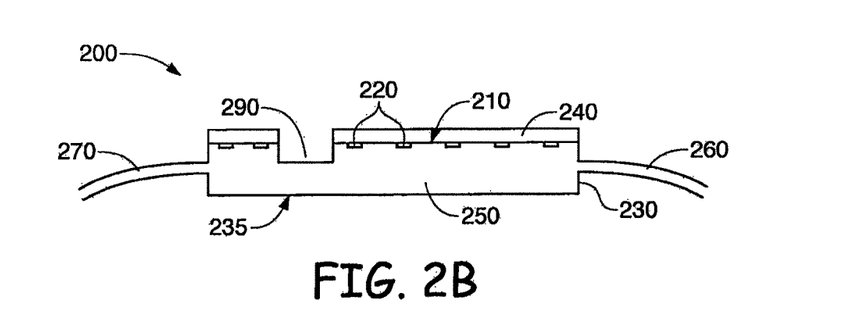
Figure 2C:
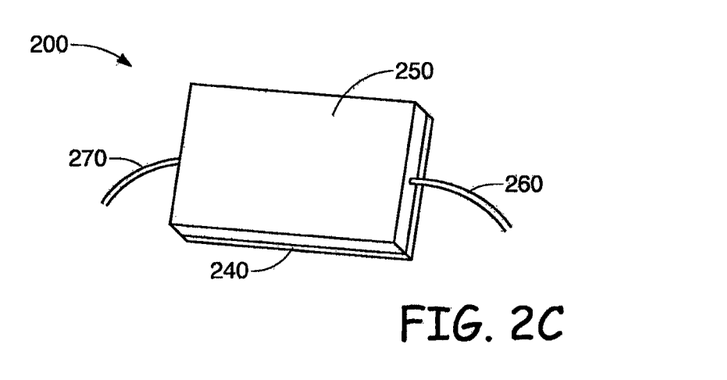

FIGS. 2A, 2B and 2C respectively show a top view, a cross-sectional view and a bottom view of an example of a temperature uniformity device 200, which can be used for LSC testing of module 100. Temperature uniformity device 200 includes an interface material 240 and a thermal conductivity device 250. The interface material 240 has a cut-out 280 or opening that is in the same location and of the same size as the cord plate 140. The thermal conductivity device 250 has two plumbing pipes 260, 270 or other flexible tubes that allow a fluid medium to be circulated and transferred between a fluid medium source 410 and the thermal conductivity device 250.

The interface material 240 has a width and length that is the same or substantially the same size as the cover plate 110 of module 100 and a thickness of approximately 0.25 mm to 5 mm, as an example, though other thicknesses can also be used. The interface material 240 can be made of a pliable thermally conductive material such as a thin thermally conductive polymer, for example, an elastomer gap filler. The elastomer gap filler can be, for example, the Tflex. 500 series thermal gap filler manufactured by Laird Technologies. The interface material 240 has a thermal conductivity in the range of 1.0 W/mK (watts per meter kelvin) to 10 W/mK and an electrical insulation property in the range of $1 \times 10^{12}$ to $1 \times 10^{16}$ ohm-cm, although polymer materials with other thermal conductivity and electrical insulation properties can be used. The Tflex 500 series thermal gap filler has a thermal conductivity of 2.8 W/mK and is electrically insulating and stable from −50° Celsius to 200° Celsius. The interface material 240 is self-adhesive or naturally tacky for attachment to the back cover plate 110 and the thermal conductivity device 250. Alternatively, the interface material 240 can be a gel coating or paste such as, for example, AI Technology Inc's cool grease CGR 7015, which is an alumina filled, electrically insulating and thermally conductive paste having good thermal transfer and adhesive properties. The CGR 7015 gel has a thermal conductivity of 2.0 W/m-°C. with an electrical resistivity of greater than $1 \times 10^{16}$ ohm-cm, and is molecularly stable up to 150° C. continuous exposure.

As shown in FIG. 2B, the thermal conductivity device 250 can have a rectangular box shape having a front side 210 that is in contact with the interface material 240, a back side 235 that is planar for stable placement on a flat surface, and side walls 230 with any suitable height, as one example, a height of one half inch can be used. The thermal conductivity device 250 has a width and length that is the same or substantially the same size as the back cover plate 110 of module 100. The thermal conductivity device 250 is made of a thermal conductive material such as molybdenum, aluminum, copper, or any other highly thermally conductive material.

The thermal conductivity device 250 is hollow and filled with a fluid medium. The fluid medium can be any liquid gel, air or gas that can be safely heated and cooled to temperatures ranging from 0° Celsius to 90° Celsius. The fluid medium can be water, ethylene glycol, nitrogen, or a gas medium such as refrigeration medium gases, or other temperature control fluid. The fluid medium entirely fills the thermal conductivity device 250. The thermal conductivity device 250 can have a plurality of sensors 220 attached to an internal surface, as shown in FIG. 2B, for monitoring the temperature of the fluid medium. Alternatively, the sensors 220 can be attached to an external surface of side walls 230.

Pipes 260, 270 are located on opposite sides of thermal conductivity device 250, although other locations can also be used. Pipe 260 injects fluid medium into the thermal conductivity device 250 and pipe 270 retrieves fluid medium from the thermal conductivity device 250. Although FIG. 2A shows one inlet pipe 260 and one outlet pipe 270, it will be appreciated that additional inlet and outlet pipes can be attached at other locations to the thermal conductivity device 250 to increase the volumetric flow rate of the fluid medium. The pipes 260, 270 can be vacuum sealed to the thermal conductivity device 250.

Figure 3:
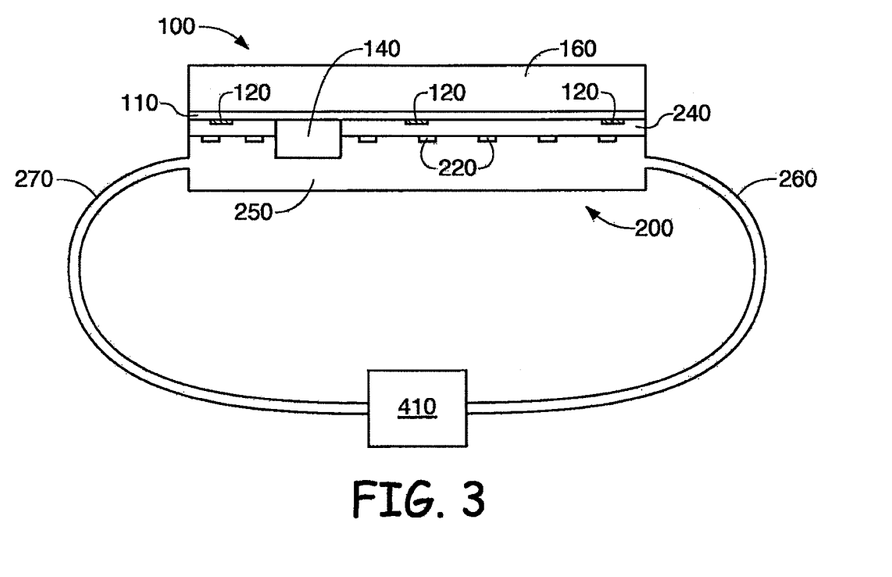
FIG. 3 shows a cross-sectional view of a photovoltaic module coupled with the temperature uniformity device of FIGS. 2A, 2B and 2C in accordance with a disclosed embodiment.

FIG. 3 shows a cross-sectional view of an exemplary photovoltaic module 100 coupled with temperature uniformity device 200. If the interface material 240 is thicker than the thickness dimensions of the cord plate 140, a recess is provided in the interface material 240. If the interface material 240 is the same thickness as the cord plate 140, then an opening 280 (FIG. 2A) is provided in the interface material 240. If the cord plate 140 is thicker than the interface material 240 then an opening 280 (FIG. 2A) is provided in the interface material 240 and a recess 290 (FIG. 2B) is provided in the thermal conductivity device 250 to accommodate the cord plate 140. In use, the interface material 240 is sandwiched between the photovoltaic module 100 and the thermal conductivity device 250 with the cord plate 140 fitting in the opening 280 (FIG. 2A) of the interface material 240 and the recess 290 (FIG. 2B) of the thermal conductivity device 250. One skilled in the art will appreciate that embodiments of the temperature uniformity device 200 can be adapted to accommodate photovoltaic modules having other external components such as one or more electrical contacts, cables and supporting frames.

In certain embodiments, the temperature uniformity device 200 is vacuum sealed to the back cover plate 110 of the photovoltaic module 100 to prevent hot or cold spots from occurring in module 100 during testing. In other embodiments, the temperature uniformity device 200 can be temporarily affixed and/or bonded to the cover plate 110. Any suitable means can be used to attach the temperature uniformity device 200 to the photovoltaic module 100 so that the device 200 is in direct contact with the back cover plate 110.

The back cover plate 110 of module 100 should be entirely or substantially entirely covered by the temperature uniformity device 200 to promote thermal conductivity between the module 100 and the temperature uniformity device 200. Heat can be conducted to and dissipated from the photovoltaic module 100 using the temperature uniformity device 200. The interface material 240 and thermal conductivity device 250 operate to control the overall temperature and temperature uniformity of the photovoltaic module 100. The electrical wires 130 of the temperature sensors 120 shown in FIG. 1C can be connected to a controller to communicate the module temperature, at each of the sensor 120 positions to the controller. Alternatively, multiple temperature sensors, like the sensors 120, can be embedded in the interface material 240 or coupled to an external surface of the thermal conductivity device 250 for sensing the temperature of the photovoltaic module 100.

Figure 4:
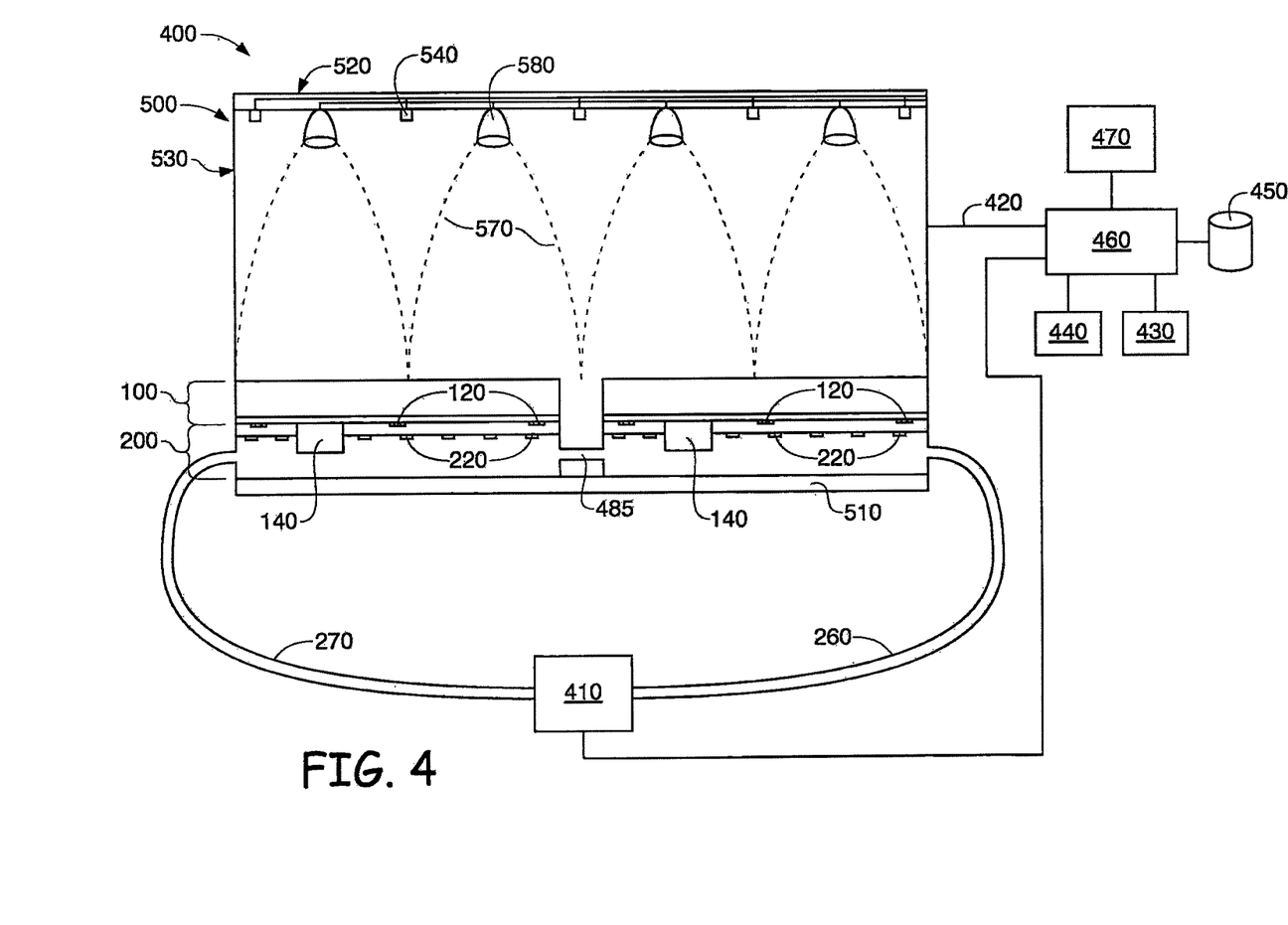
FIG. 4 is a diagram of a light soaking system in accordance with a disclosed embodiment.

FIG. 4 is a diagram of a light soaking system 400. Light soaking system 400 includes a light soaking chamber 500, a fluid medium source 410, a controller 460, communication lines 420 to the controller 460, a data acquisition device 470, a storage device 450, a display 430 and an input device 440. Controller 460 can be a computer with a processor or a programmable logic controller (PLC). The fluid medium source 410 has an adjustable flow valve that can regulate the fluid medium flow. The fluid medium source 410 can be a compressed air conditioner unit or a process chiller such as the P-Series Chiller manufactured by ArctiChill, or other suitable device for cooling the fluid medium.

Light soaking chamber 500 has a bottom chamber platform 510, a top chamber ceiling 520 and side chamber walls 530. Light soaking chamber 500 can hold a plurality of photovoltaic modules 100. Each photovoltaic module 100 can be coupled to a respective temperature uniformity device 200. Two photovoltaic modules 100 can be arranged adjacent to each other in chamber 500 as shown in FIG. 4. The chamber 500 however can be sized to fit a 2 by 3 configuration of a plurality of photovoltaic modules 100 or any other configuration. As shown in FIG. 4, the bottom side of the temperature uniformity device 200 is flat and in full contact with the top surface of the chamber platform 520.

A collection of light sources 580 are attached to the ceiling 520 of light soaking chamber 500 for providing simulated light exposure 570 to the photovoltaic modules 100 during a testing procedure, such as an accelerated life testing procedure. The light sources 580 can be high power metal halide lamps, gas lasers, Xenon discharge lights or any other light source that can illuminate the photovoltaic modules 100 in the chamber 500. The light sources 580 are connected to and controlled by controller 460 via communication lines 420. Controller 460 is configured to turn on/off and adjust the illumination intensity (dim or brighten) of each light source 580 according to a testing procedure. Light sources 580 can be filtered or shaded to control the optical intensity and direct the intensity to a target area of the photovoltaic modules 100 or chamber 500.

Chamber temperature sensors 540 can be attached to the chamber ceiling 520 or any other suitable location in the chamber 500 to provide a temperature measurement for the ambient temperature within the chamber 500. Sensors 540 can be an optical sensor such as a laser sensor, an infrared sensor, or camera. Electrical wires from the sensors 540 connect to the communication lines 420 for sending chamber 500 temperature readings to the controller 460.

The temperature sensors 120 of the photovoltaic modules 100 are also connected to the controller 460 through the communication lines 420. The controller 460 can be configured to receive temperature readings from the temperature sensors 120 of the photovoltaic module 100 at set time intervals such as every thirty seconds or every minute. Controller 460 analyzes the photovoltaic module temperature readings to determine whether the overall temperature of the photovoltaic module 100 is within an acceptable temperature range. For example, an acceptable temperature range for the photovoltaic module 100 can be +/−1° Celsius or +/−2° Celsius of a set point temperature. Controller 460 also analyzes the photovoltaic module temperature readings to determine whether the temperature uniformity of the photovoltaic module 100 is within an acceptable temperature deviation. An example of an acceptable temperature deviation for the photovoltaic module 100 can be a maximum of +/−4° Celsius across all the temperature readings; however, other temperature range deviations can also be acceptable.

The acceptable temperature range and acceptable temperature deviation values can be operating parameters stored in the storage device 450 as part of an accelerated life testing procedure. A user can specify the acceptable temperature range and acceptable temperature deviation values, a test duration, illumination intensity amount and any other operating and test parameters for an accelerated life testing session using input device 440 and display 430. The user can also identify and program which of the temperature sensors 120 are considered in determining the overall temperature and the temperature uniformity of the module 100. For example, if a particular photovoltaic cell or region of the module 100 has a short-circuit or is defective for any reason, the user can specify that any temperature sensor 120 near this cell or within this region is not be included in determining the overall temperature and the temperature uniformity of the module 100. The user can select the one or more temperature sensors 120 to be considered using input device 440 and display 430.

The fluid medium source 410 sets the fluid medium at a temperature set by the controller 460. The fluid medium source 410 can control the temperature of the fluid medium to the acceptable temperature rang; such as +/−1° Celsius or +/−2° Celsius of the set point temperature; however, other temperature ranges can also be used Each temperature uniformity device 200 in chamber 500 can be connected to its own fluid medium source 410 or to a common, external fluid medium source located outside of light soaking chamber 500. Alternatively, as shown in FIG. 4, two or more thermal conductivity devices 250 can be connected to each other using plumbing pipes 485 to decrease the number of plumbing pipes connected to the fluid medium source 410.

When the overall temperature or the temperature uniformity of the photovoltaic module 100 is not within the respective acceptable temperature range or acceptable temperature deviation, the controller 460 sends a signal to the fluid medium source 410 to increase the flow of the fluid medium into the thermal conductivity device 250 through the adjustable flow valve. The controller 460 can also send a signal to the fluid medium source 410 to decrease the temperature of the fluid medium exiting the fluid medium source 410.

When the fluid medium source 410 receives the signal to increase the flow of the fluid medium from the controller 460, the fluid medium source 410 sends fluid medium into the thermal conductivity device 250 through the plumbing pipe 260. Simultaneously, fluid medium inside the thermal conductivity device 250 is delivered to the fluid medium source 410 for temperature control via the plumbing pipe 270. The controller 460 is configured to send a signal to decrease the fluid flow when the overall temperature or the temperature uniformity of the photovoltaic module 100 is within the respective acceptable temperature range or acceptable temperature deviation. Alternatively, the controller 460 is configured to stop the fluid flow when a predetermined amount of fluid medium has been exchanged between the fluid medium source 410 and the thermal conductivity device 250. The controller 460 can also stop the fluid flow after a predetermined time period such as one minute.

The electrical and temperature data can be measured during and after a testing session lithe data is collected during the testing session, the electrical wires 141, 142 (FIG. 1B) of the module 100 are connected to the controller 460 via communication lines 420. Electrical and temperature data measurements such as current-voltage (I-V), capacitance-voltage (C-V), capacitance-frequency (C-F) and spectral response (SR) collected intermittently from the photovoltaic module 100 are sent to the controller 460 via communications lines 420 and stored in the storage device 450. In addition to the temperature sensors 120, additional sensors attached to the ceiling 520 of the light soaking chamber 500 for measuring the surface temperature of the photovoltaic module 100 can be used to collect the temperature data. If the electrical and temperature data is collected after the testing session, the electrical wires 141, 142 of the module 100 are not connected to the controller 460.

Electrical characteristics of multiple photovoltaic modules 100 undergoing sunlight exposure can be manually or remotely controlled using programmable electronic loads. The programmable electronic loads can be stored in the storage device 450 or inputted by a user using input device 440. Input device 440 can be a keyboard connected to the controller 460 or a remote device that can communicate with the controller 460. Data acquisition device 470 can be a computer or any other processing unit for analyzing the electrical and temperature data. Data acquisition device 470 can generate reports of the analysis during and after a test session.

Figure 5:
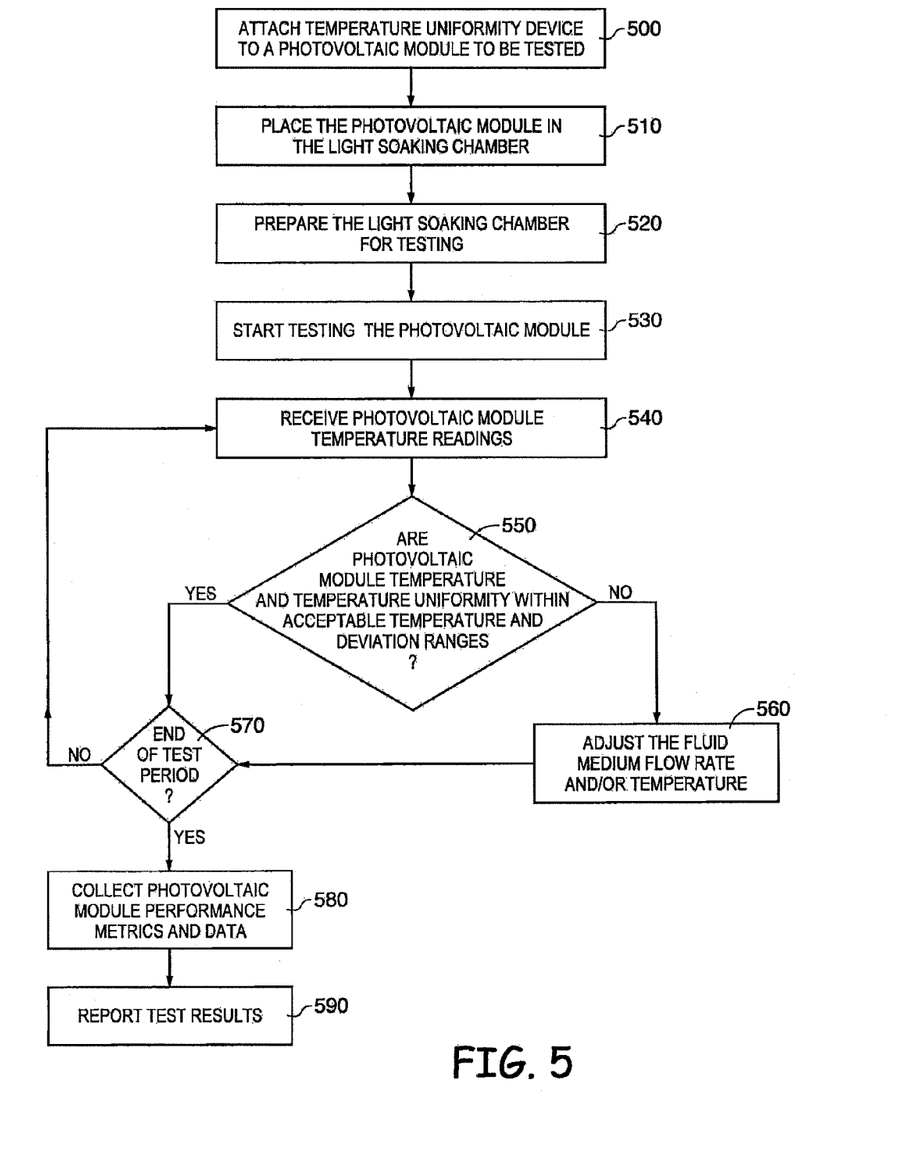
FIG. 5 is a flowchart for testing an exemplary photovoltaic module coupled to a temperature uniformity device in accordance with a disclosed embodiment.

FIG. 5 is a flowchart for testing a photovoltaic module 100 in the light soaking chamber 500. At step 500, a user attaches a temperature uniformity device 200 to each of the photovoltaic modules 100 to be tested. The interface material can be preattached to the thermal conductivity device of the temperature uniformity device 200 to facilitate quicker preparation of the photovoltaic modules 100 for testing. The temperature uniformity device 200 can be preattached to an external fluid medium source 410. Each photovoltaic module 100 can be vacuum sealed to the temperature uniformity device 200 prior to placement in the chamber 500 by the user at step 510. Once the temperature uniformity device 200 is attached to the photovoltaic module 100, the controller 460 commands the fluid medium source 410 to fill the thermal conductivity device of the temperature uniformity device 200 with a fluid medium having a temperature within the acceptable temperature range. The thermal conductivity device can also be filled with the fluid medium prior to attachment to the photovoltaic module 100.

At step 520, the light soaking chamber 500 is prepared for testing the photovoltaic modules 100. The preparation of the chamber 500 can be carried out according to a programmable testing program by the controller 460 of the light soaking system 400. The testing program can be an accelerated life testing procedure that is part of a standalone test of the photovoltaic modules 100 or as part of a photovoltaic module production line. The testing conditions can be set to the so-called Standard Test Conditions (STC), which corresponds to 1000 W/m$^2$, 25° Celsius set point temperature, with a reference solar spectral irradiance called Air Mass 1.5 (AM 1.5). The operating conditions and test parameters such as the duration of the test period, the set point temperature, and the initial fluid medium flow rate can be prestored in the storage device 450 or provided to the controller 460 using input device 440 and display 430. The chamber 500 or dedicated room can be prepared by ramping up the temperature of the chamber 500 or room to the predetermined set point temperature using the light sources 580 or an external heating device. Temperature readings from sensors 540 can be used by the controller 460 to monitor the temperature of the chamber 500.

At step 530, the controller 460 starts the testing period and the photovoltaic modules 100 are illuminated by the light sources 580. The light sources 580 are adjusted (dimmed and brightened) by the controller 460 according to the testing procedure. The controller 460 commands the fluid medium source 410 to allow fluid medium to flow into and out of the thermal conductivity device 250 at an initial flow rate. The fluid medium exiting the fluid medium source 410 is set to a temperature within the acceptable temperature range.

At step 540, the controller 460 monitors the temperature and temperature uniformity of the photovoltaic modules 100 by receiving temperature readings from the sensors 120. The controller 460 receives temperature readings from the photovoltaic modules 100 at set time intervals such as every 30 seconds or every minute. At step 550, the controller 46 analyzes the photovoltaic module temperature readings to determine whether the overall temperature of the photovoltaic module 100 is within the acceptable temperature range, which is +/−2° Celsius of the set point temperature. The photovoltaic module temperature readings are averaged and compared with the acceptable temperature range to determine if the average temperature is within the acceptable temperature range. If the average photovoltaic module temperature reading is determined at step 550 to be outside the acceptable temperature range, the controller 460 commands the fluid medium source 410 to increase the fluid medium flowing into the thermal conductivity device 250 at step 560. The fluid medium exiting the fluid medium source 410 is set to a temperature within the acceptable temperature range. Alternatively, if the average photovoltaic module temperature reading is above the acceptable temperature range, the controller 460 commands the fluid medium source 410 to cool the fluid medium exiting the source 410 to below the set point temperature, e.g., −1° Celsius or −2° Celsius of the set point temperature.

Controller 460 also analyzes the photovoltaic module temperature readings to determine whether the temperature uniformity of the photovoltaic module 460 is within the acceptable temperature deviation, which is a maximum of +/−4° Celsius. Pairs of photovoltaic module temperature readings are compared to determine a maximum difference between any pair of temperature readings. The controller 460 then determines whether this maximum difference value is within the acceptable temperature deviation. If the maximum difference value of the temperature readings is determined at step 550 to be outside the acceptable temperature deviation range, the controller 460 commands the fluid medium source 410 to increase the fluid medium flowing into the thermal conductivity device 250 at step 560. The fluid medium exiting the fluid medium source 410 is set to a temperature within the acceptable temperature range.

When the fluid medium source 410 receives the command to increase the fluid medium flow, the fluid medium source 410 adjusts its flow valve to increase the rate of the fluid medium flowing into and out of the thermal conductivity device 250. The fluid medium flow can be increased and decreased gradually. For example, the flow of fluid medium can be adjusted to increase at a rate of 20% every minute. The controller 460 can command the fluid medium source 410 to decrease the fluid medium flow to the initial flow rate after a predetermined volume of fluid medium has been pumped into and/or out of the thermal conductivity device 250. Alternatively, the fluid medium flow can be decreased after a predetermined time period. The fluid medium flow can also be configured to decrease when the photovoltaic module temperature readings are within the acceptable temperature range and the acceptable temperature deviation.

At step 570, the controller determines if the testing period has ended. If the testing period has not ended, the controller 460 waits for the next set of photovoltaic module temperature readings. Once the testing period has ended, the controller 460 collects electrical data and temperature data for the photovoltaic modules 100 and sends the data to the data acquisition device 470 for analysis at step 580. The controller 460 collects electrical and temperature data measurements such as current-voltage (I-V), capacitance-voltage (C-V), capacitance-frequency (C-F) and spectral response (SR) intermittently on the photovoltaic module. The data acquisition device 470, at step 590, can generate summary reports of the photovoltaic module 100 performance changes in the short circuit current, open-circuit voltage, fill factor and cell efficiency, for example.

The testing procedure may also be configured and started using a remote device such as a laptop that can communicate with controller 460. Testing parameters such as the set point temperature, the length of the testing period, the initial fluid medium flow rate, the acceptable photovoltaic module temperature and deviation ranges, and the selection of temperature sensors that will be considered in determining a photovoltaic module's overall temperature and temperature uniformity can be configured using the remote device.

Figure 6A:
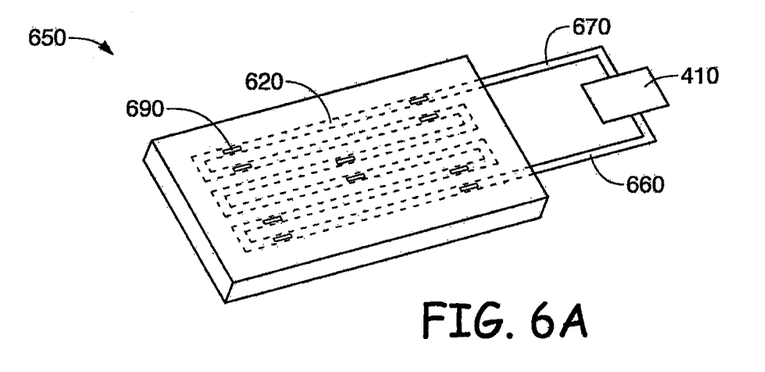
FIG. 6A is a top view of a thermal conductivity device in accordance with a disclosed embodiment.

FIG. 6A is a top view of a thermal conductivity device 650 in accordance with another embodiment. The differences between thermal conductivity devices 250 and 650 are explained below. Unlike the hollow structure of the thermal conductivity device 250, the thermal conductivity device 650 is a solid metal plate made of a thermal conductive material such as molybdenum, aluminum, copper, or any other highly thermally conductive material. Embedded inside the thermal conductivity device. 650 is a continuous coolant line 620 that starts from the input pipe 670 and weaves back and forth inside the thermal conductivity device 650 to the output pipe. 660 in a serpentine-like manner. The coolant line 620 can be drilled out of the thermal conductivity device 650, although other ways of forming the coolant line 620 inside the thermal conductivity device 650 can be employed. The coolant line 620 has a length of approximately 24 feet and a diameter of about 1-inch, although other dimensions are also possible. The input 670 and output 660 pipes are connected to a fluid medium source 410. A fluid medium enters the coolant line 620 through the input pipe 670 and exits via the output pipe 660. Attached at various locations on top of the thermal conductivity device 250 and above the coolant line 620 are multiple temperature sensors 690. Temperature sensors 690 are similar to sensors 220 (FIG. 2B) for monitoring the temperature of the fluid medium inside the coolant line 620.

Figure 6B:
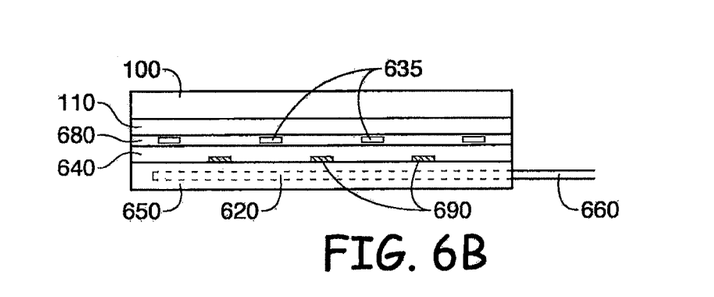
FIG. 6B shows a cross-sectional view of an exemplary photovoltaic module coupled with a temperature uniformity device in accordance with a disclosed embodiment.

FIG. 6B shows a cross-sectional view of the exemplary photovoltaic module 100 coupled with a temperature uniformity device 600. Like the temperature uniformity device 200, the temperature uniformity device 600 has an interface material 640 that is sandwiched between the photovoltaic module 100 and the thermal conductivity device 650. The thermal conductivity device 650 is approximately 2-inches thick and has the same width and length as the back cover plate 110 of the exemplary photovoltaic module 100. The differences between temperature uniformity devices 200 and 600 are explained below. Multiple temperature sensors 635 similar to the sensors 120 (FIG. 1B) are embedded in the interface material 640 for sensing the temperature of the photovoltaic module 100. The photovoltaic module 100 does not show a cord plate attached to the back cover plate 110. However, it will be appreciated that the shape and location of the coolant line 620 inside the temperature conductivity device 650 and the interface material 640 can be modified to accommodate the cord plate 140 of the exemplary photovoltaic module 100. The interface material 640 can be a pliable thermally conductive material such as, for example, a thermally conductive polymer or a gel coating or paste 680. The thermally conductive polymer can be, for example, an elastomer gap filler, for example, the Tflex 500 series thermal gap filler manufactured by Laird Technologies. The gel coating or paste 680 can be, for example, AI Technology Inc's cool grease CGR 7015, which is an alumina filled, electrically insulating and thermally conductive paste having good thermal transfer and adhesive properties. The CGR 7015 gel has a thermal conductivity of 2.0 W/m-° C. with an electrical resistivity of greater than $1 \times 10^{16}$ ohm-cm, and is molecularly stable up to 150° C. continuous exposure. It shall be appreciated that the interface material 640 can be thermally conductive polymer with a gel coating on the side of the interface material 640 that contacts the back cover plate 110.

Figure 7:
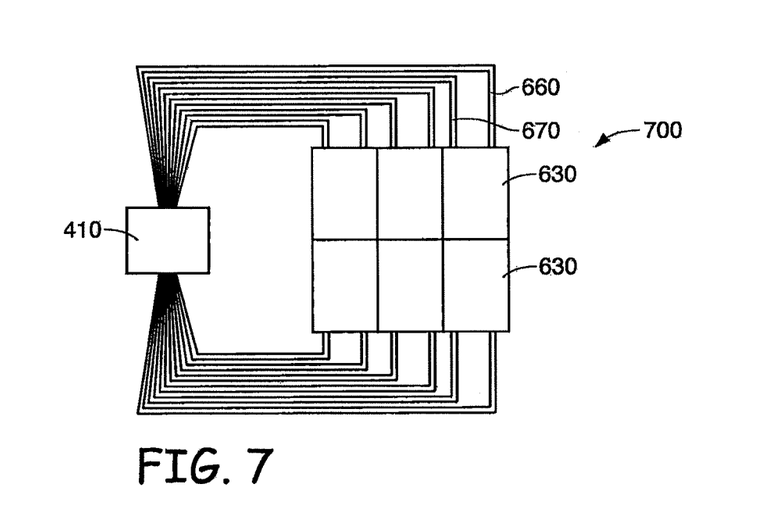
FIG. 7 shows a top view of a light soaking chamber for testing a plurality of photovoltaic modules in accordance with a disclosed embodiment.

FIG. 7 shows a top simplified view of a light soaking chamber 700 that can test six exemplary photovoltaic modules 100 at once. Differences between the light soaking chambers 700 and 500 are explained below. The photovoltaic modules 100 are placed in two rows, each row having three modules 100. Because the input 670 and output 660 pipes of each module 100 are located on the same side, the modules 100 can be placed next to each other as shown in FIG. 7. Each of the input 670 and output 660 pipes are connected to a single fluid medium source 410, although multiple fluid medium sources 410 can also be used.

It will be appreciated that the light soaking chamber 700 can be used in a light soaking system similar to the light soaking system 400 (FIG. 4). It will also be appreciated that the testing process shown in FIG. 5 can be modified to test photovoltaic modules 100 in the light soaking chamber 700. For example, at step 500, each photovoltaic module 100 to be tested is coupled to a temperature uniformity device 600. At step 510, the photovoltaic modules 100 are placed in the light soaking chamber 700 and the controller 460 commands the fluid medium source 410 to fill the coolant line 620 with a fluid medium having a, temperature within the acceptable temperature range.

Figure 8A:
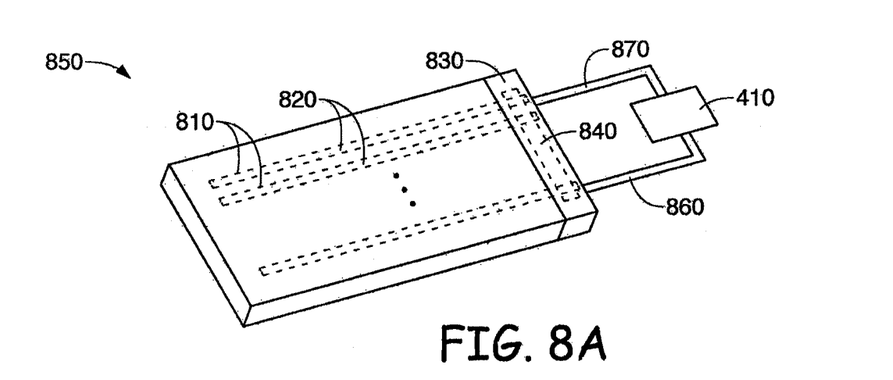
FIG. 8A is a top view of a thermal conductivity device in accordance with a disclosed embodiment.

FIG. 8A is a top view of a thermal conductivity device 850 in accordance with another embodiment. The thermal conductivity device 850 uses heat pipes 820 to manage the transfer of heat between a photovoltaic module and a heat exchanger. Like the thermal conductivity device 650, the thermal conductivity device 850 is a solid metal plate made of a thermal conductive material such as molybdenum, aluminum, copper, or any other highly thermally conductive material. The differences between thermal conductivity devices 850 and 650 (FIG. 6A) are explained below. The thermal conductivity device 850 has a series of elongated spaces 810 that are parallel to each other. Each elongated space 810 is approximately one-inch in diameter and runs about the length of the thermal conductivity device 850 as shown in FIG. 8A. The spaces 810 can be drilled out of the thermal conductivity device 850, although other ways of forming the spaces 810 inside the thermal conductivity device 850 can be employed. A heat pipe 820 having a diameter of approximately one-inch is inserted into each space 810, although heat pipes and spaces of other diameters can be employed. All air is removed from the heat pipe 820 before filling the pipe 820 with a coolant such as a refrigerant or any other fluid that can safely operate from 0° to 90° Celsius. The heat pipes 820 are a few inches longer than the spaces 810 such that when a heat pipe 820 is inserted into a space 810, a portion of the heat pipe 820 extends out of the space 810 as shown in FIG. 8A. A heat exchanger block 830 is attached to one end of the thermal conductivity device 850 and has a cavity 840 for holding the portion of the heat pipe 820 that extends out of the space 810. The heat pipes 820 and the heat exchanger block 830 are made of a material with high thermal conductivity such as copper or aluminum. The input 870 and output 860 pipes of the heat exchanger block 830 are connected to a fluid medium source 410. A fluid medium from the fluid medium source 410 is pumped through the cavity 840 of the heat exchanger block 830 via the input 870 and output 860 pipes.

Figure 8B:
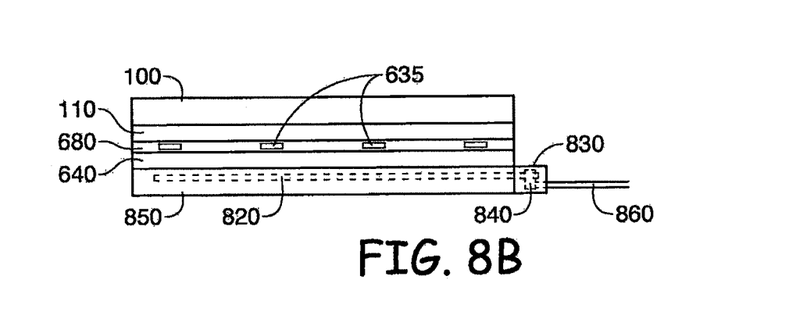
FIG. 8B shows a cross-sectional view of an exemplary photovoltaic module coupled with a temperature uniformity device in accordance with a disclosed embodiment.

FIG. 8B shows a cross-sectional view of the exemplary photovoltaic module 100 coupled with a temperature uniformity device 800. The differences between temperature uniformity devices 600 and 800 are explained below. As described above, the fluid medium source 410 can control the temperature of the fluid medium to the acceptable temperature range, such as +/−1° Celsius or +/−2° Celsius of the set point temperature; however, other temperature ranges can also be used. In use, when the temperature of the photovoltaic module 100 increases, the coolant inside the heat pipes 820 evaporates and increases the vapour pressure inside the cavities of the heat pipes 820. The latent heat of evaporation absorbed by the vaporization of the coolant reduces the temperature of the photovoltaic module 100. The excess vapour is transferred to the end of the heat pipe 820 that is inside the heat exchanger block 830. As the fluid medium is continuously pumped through the heat exchanger block 830 during testing of the photovoltaic module 100, the temperature of the fluid medium inside the heat exchanger block 830 rises due to the heat transfer from the heat pipes 820. The heated fluid medium exits though the output 860 pipe to the fluid medium source 410 for cooling. The interface material 640 and gel layer 680 may be placed between the back cover plate 110 of the photovoltaic module 100 and the thermal conductivity device 850. It will be appreciated that the photovoltaic module 100 coupled with the temperature uniformity device 800 can be tested in the light soaking chamber 700 using a light soaking system similar to the light soaking system 400 (FIG. 4).

While disclosed embodiments have been described in detail, it should be readily understood that the invention is not limited to the disclosed embodiments. For example, it should be appreciated that the disclosed embodiments of the temperature uniformity device can be coupled to objects other than a photovoltaic module for controlling the temperature and the temperature uniformity of the object. Rather the disclosed embodiments can be modified to incorporate any number of variations, alterations, substitutions or equivalent arrangements not heretofore described.

What is claimed as new and desired to be protected by Letters Patent of the United States is:

1. A light soaking system comprising:
   a light soaking chamber comprising:
     a surface for receiving a photovoltaic module to be tested;
     a light source for illuminating the photovoltaic module;
     a first temperature sensor for measuring a temperature of the chamber; and
   a temperature uniformity device comprising:
     a thermal conductivity device for holding a fluid medium; and
     an interface material made of a pliable thermally conductive material attached on one side to a front surface of the thermal conductivity device for coupling on the other side to the photovoltaic module to be tested when a photovoltaic module is on the temperature uniformity device, wherein the photovoltaic module to be tested includes a plurality of second photovoltaic temperature sensors affixed thereto and the interface material is configured, when the photovoltaic module is on the temperature uniformity device, to be between the thermal conductivity device and the photovoltaic module and maintain direct contact with the photovoltaic module, the plurality of second photovoltaic temperature sensors, and the thermal conductivity device;
   a fluid medium source connected to the thermal conductivity device;
   a plurality of third temperature sensors configured such that the third temperature sensors are located between the fluid medium and the interface material when the thermal conductivity device is holding fluid medium; and
   a controller configured to monitor at least one temperature of the plurality of second photovoltaic temperature sensors and/or third temperature sensors and a temperature uniformity of the photovoltaic module and to adjust a temperature of the fluid medium by adjusting a flow rate of the fluid medium through the thermal conductivity device and/or by adjusting a temperature of the fluid medium exiting the fluid medium source.

2. The light soaking system of claim 1, wherein the thermal conductivity device is formed of at least one of molybdenum, aluminum, copper or combination thereof.

3. The light soaking system of claim 1, wherein the interface material has a thermal conductivity property in the range of about 1.0 W/mK to about 10 W/mK.

4. The light soaking system of claim 1, wherein the interface material has an electrical insulation property in the range of about $10^{12}$ to about $10^{16}$ ohm-cm.

5. The light soaking system of claim 1, wherein one or more temperature measuring sensors are embedded in the interface material for monitoring the temperature of the photovoltaic module.

6. The light soaking system of claim 1, wherein one or more temperature measuring sensors are attached to the thermal conductivity device for monitoring the temperature of the thermal conductivity device.

7. The light soaking system of claim 1, wherein the thermal conductivity device further comprises a plurality of heat pipes for cooling the thermal conductivity device and a heat exchanger attached to one end of the thermal conductivity device, the heat exchanger having a cavity for holding an end portion of each of the plurality of heat pipes and further comprising at least two pipes connected to the cavity for circulating a fluid medium through the cavity.

8. The light soaking system of claim 1, wherein the controller is configured to accept temperature readings from the plurality of first, second, and third temperature sensors, and to adjust the flow rate of the fluid medium based on the temperature readings from the plurality of temperature sensors.

9. The light soaking system of claim 1, wherein the interface material comprises a gel coating.

10. The light soaking system of claim 9, wherein the gel coating is an alumina filled, electrically insulating and thermally conductive paste.

11. The light soaking system of claim 1, wherein the fluid medium comprises a fluid that can be heated and cooled to temperatures ranging from 0° Celsius to 90° Celsius.

12. The light soaking system of claim 11, wherein the fluid medium is a liquid selected from the group consisting of water, ethylene glycol or liquid nitrogen.

13. The light soaking system of claim 11, wherein the fluid medium is a gas.

14. The light soaking system of claim 11, wherein a plurality of sensors are attached to a wall of the thermal conductivity device for monitoring the temperature of the fluid medium.

15. A testing method for a photovoltaic module, comprising the steps of:
illuminating a photovoltaic module having a plurality of first photovoltaic temperature sensors affixed thereto, the photovoltaic module being coupled to a temperature uniformity device, the temperature uniformity device having a thermal conductivity device holding a fluid medium and an interface material made of a pliable thermally conductive material attached on one side to a front surface of the thermal conductivity device for coupling on the other side to the photovoltaic module, wherein the interface material is configured to be between the thermal conductivity device and the photovoltaic module and maintain direct contact with the photovoltaic module, the plurality of first photovoltaic temperature sensors, and the thermal conductivity device, the temperature uniformity device further including a plurality of second temperature sensors configured such that the second temperature sensors are located between the fluid medium and the interface material; and
monitoring a temperature and a temperature uniformity of the photovoltaic module at a plurality of points on the photovoltaic module using the plurality of first photovoltaic temperature sensors and the plurality of second temperature sensors.

16. The testing method of claim 15, further comprising vacuum sealing the temperature uniformity device to a cover plate of the photovoltaic module.

17. The testing method of claim 15, further comprising adjusting a flow rate of the fluid medium through the thermal conductivity device based on a predetermined time period.

18. The testing method of claim 15, wherein the monitoring step comprises analyzing temperature readings from at least one of the plurality of first and second temperature sensors.

19. The testing method of claim 18, further comprising adjusting a flow rate of the fluid medium through the thermal conductivity device based on temperature readings from at least one of the plurality of first and second temperature sensors.

20. The testing method of claim of claim 19, wherein the flow rate of the fluid medium through the thermal conductivity device is increased if the temperature difference between at least two of the plurality of first and second temperature sensors is greater than or equal to about four degrees Celsius from each other.

21. The testing method of claim of claim 19, wherein the flow rate of the fluid medium through the thermal conductivity device is increased if the absolute value of the temperature readings from at least one of the plurality of first and second temperature sensors is greater than or equal to about two degrees Celsius from a set point temperature.

22. The testing method of claim of claim 21, wherein the set point temperature is about 25 degrees Celsius.

* * * * *